United States Patent
Jonjic

[19]

[11] Patent Number: 5,989,024
[45] Date of Patent: Nov. 23, 1999

[54] DENTAL PARALLELOMETER

[76] Inventor: Leo Jonjic, Primorska 31, 51414 Ika-Icici, Croatia

[21] Appl. No.: 08/974,712

[22] Filed: Nov. 19, 1997

[30] Foreign Application Priority Data

Aug. 25, 1997 [HR] Croatia ................................ P970451A

[51] Int. Cl.$^6$ ....................................................... A61C 3/02
[52] U.S. Cl. .................................................................. 433/76
[58] Field of Search .................................................. 433/76

[56] References Cited

U.S. PATENT DOCUMENTS

| | | | |
|---|---|---|---|
| 3,254,413 | 6/1966 | Suga | 433/76 |
| 3,346,959 | 10/1967 | Fridge | 433/76 |
| 3,375,584 | 4/1968 | Cowan | 433/76 |
| 5,017,139 | 5/1991 | Mushabac | 433/76 X |
| 5,332,391 | 7/1994 | Jermyn | 433/76 |
| 5,575,646 | 11/1996 | Giannella | 433/76 |

*Primary Examiner*—Nicholas D. Lucchesi

[57] ABSTRACT

The present invention provides an apparatus for cooperating with a powered tool having a work imparting component having a longitudinal axis so as to maintain the longitudinal axis at substantially constant angles in the X-Y, Y-Z and Z-X planes, as defined in part by the X, Y and Z axes while the powered tool is caused to move through a volume of space. The apparatus includes: an adjustable arm having two ends; a clamp arrangement (14-16) for fixing the powered tool to one of the two ends; and, a base (1-2) fixable to a work piece, attached to the other of the two ends, for supporting the adjustable arm (4-13) and the clamp arrangement (14-16). The adjustable arm further includes: a first portion (4, 5) having two ends, for enabling vertical displacement of the longitudinal axis relative to the Y axis; a second portion (7, 9 and 10-13) having two ends, for supporting the clamp arrangement (14-16); and, a third portion (6, 8) for movably fixing one end of the first portion to one end of the second portion. The third portion further includes: a first arrangement (8) for horizontal extension and retraction of the second portion relative to the X-Z plane; and, a second arrangement (6) for enabling revolution of the clamp arrangement about the third portion.

13 Claims, 4 Drawing Sheets

DENTAL PARALLELOMETER

BACKGROUND OF THE INVENTION

Broadly, the instant invention relates to an apparatus for maintaining the axis of the work imparting portion of a powered tool at a substantially constant angle. Specifically, the invention relates to an apparatus for maintaining the axis of the drill bit of a dental drill at a substantially constant angle while the apparatus is affixed to, and operating on, a palatal prosthesis.

THE PRIOR ART

Broadly, various devices of the prior art have been proposed for orienting the work imparting components of powered tools.

For instance: U.S. Pat. No. 5,413,440 to Willson, et al, teaches a unit for the support of power tools and the like, that includes: a base; an elongate post affixed at one end to the base in a normally upright attitude, the post having a toothed rack spaced upwardly from the base and extending longitudinally thereon, and the post being of generally circular cross section, at least in a lower section of its length lying between the base and the rack; a first rigid arm supported for longitudinal movement on the post; and a second, articulated arm supported for longitudinal movement on the post; both of the arms having opposite end portions with clamping means and post-engaging means thereon, respectively; the clamping means defining an opening of variable effective cross section for receiving and clampingly engaging therein bodies of different sizes; and the post-engaging means comprising a mounting part having an axial passage therethrough for slidably receiving the post, a pinion mounted on the mounting part and operatively engageable with the rack for raising and lowering the associated arm, and securing means for securing the associated arm at selected levels on the post, the mounting part of at least one of the arms being of sufficiently small axial length to pass between the base and the rack and the passage therethrough being of generally circular cross section, the one arm thereby being rotatable on the post with the mounting part and the base section thereof, respectively, in mutual registration.

More specifically, various types of parallelometer devices are known in the dentistry arts.

For instance, U.S. Pat. No. 3,760,504 to Ljubarsky, et al, teaches a parallelometer that includes a base; a platen for a jaw pattern being secured to the base; a support mounted on the base; a chuck fastened to the support; a two-armed hinged lever interconnecting the chuck and platen for relative movement perpendicularly to the axis of the chuck and towards each other; a sleeve secured in the chuck; a socket in the sleeve for mounting a tooth-marking working tool; means connected to the sleeve extending parallel to the working tool; a system of articulated rods extending between and being fastened to the last-mentioned means and the sleeve, the rods adapted to be aligned with the tooth axes in the jaw pattern and forming a rhomboid structure with changeable angles, one of the diagonals of the rhomboid structure being directed along the axis of the working tool in the sleeve.

U.S. Pat. No. 4,998,881 to Lauks, teaches a jaw-surgery instrument for boring implant cavities, that includes: a drill provided with a boring tool; a guide sleeve receiving the tool and slidably guiding the tool along an axis of the guide sleeve; a guide-sleeve template conforming in shape to a shape of a jaw region of a patient to receive an implant and holding the guide sleeve for positioning the guide sleeve in the jaw region of the patient, the guide sleeve being formed with an end turned toward the drill and an end turned away from the drill and received in the template, the end turned toward the drill being formed with a radially outwardly extending annular flange; and a slide extending upwardly from the annular flange and guiding the drill relative to the guide sleeve.

U.S. Pat. No. 4,824,367 to Rosenstiel, et al, teaches a parallel alignment indicator for a dental handpiece, that includes: angle-indicator means for generating electrical angle signals representative of an angular orientation of an axis of a cutter held, in operation, by a dental handpiece; setting means for setting electrical reference signals representing a position of a pre-selected axis; and warning means arranged to generate a warning when a relationship between the electrical angle signals and the electrical reference signals falls outside predetermined limits.

It would be advantageous to provide a parallelometer device that offers substantially more degrees of freedom, so as to enable the practitioner to quickly and easily adjust the device to accomodate substantially any condition which may arise in normal practice.

More specifically, it would be advantageous to provide a dental parallelometer device that offers substantially more degrees of freedom, so as to enable the dental practitioner to quickly and easily adjust the device to accomodate substantially any condition which may arise in the typical practice of dentistry.

SUMMARY OF THE INVENTION

The instant invention in large part solves the problems of the prior and fulfills a long felt need by providing a new and improved parallelometer type device.

Broadly the instant invention provides an apparatus for maintaining the axis of the work imparting portion of a powered tool at a substantially constant angle.

More specifically, the invention provides an apparatus for maintaining the axis of the drill bit of a dental drill at a substantially constant angle while apparatus is affixed to, and operating on, a palatal prosthesis. Typically, this angle is from about 8° to about 10°, but can range from about 3° to about 15°.

Also contemplated by the invention is a method of using the instant apparatus.

Here are the more important features of the invention as broadly outlined, in order that the detailed description that follows may be better understood; and in order for the present contribution to the art may be better appreciated. There are additional features of the invention that will be described hereinafter and which form the subject matter of the appended claims. Those of ordinary skill in the art will appreciate that the conception upon which this disclosure is based may readily be utilized as a basis for the designing of other structures, methods and systems for carrying out the several purposes of the instant invention. It is important, therefore, that the claims be regarded as including such equivalent constructions insofar as they do not depart from the spirit and scope of the instant invention.

Further, the purpose of the instant abstract is to enable the U.S. Patent and Trademark office and the public generally, and especially the scientists, engineers and practitioners in the art who are not familiar with patent or legal terms or phraseology, to determine quickly from a cursory inspection of it, the technical disclosure of the patent application. The abstract is neither intended to define the invention of the instant patent application, which is measured by the claims, nor is it intended in any manner to be limiting as to the scope of the instant invention.

In light of the foregoing, it is therefore an object of the instant invention to provide a new and improved apparatus that has all of the advantages of the prior art and none of its disadvantages.

It is another object of the instant invention to provide a new and improved apparatus that may be easily and efficiently manufactured and marketed.

It is another object of the instant invention to provide a new and improved apparatus that is of a durable and reliable construction It is another object of the instant invention to provide a new and improved apparatus that can be manufactured at low cost with regard to both labor and materials, and that accordingly can be sold at a substantially lower cost than those similar devices currently available to the prior art, thus promoting commerce.

It is a further object of the instant invention to provide a new and improved apparatus that provides at least some of the advantages of the prior art schemes, while simultaneously eliminating at least some of the disadvantages of them.

Other objects, features, and advantages of the instant invention, in its details of construction and arrangement of parts, will be seen from the above, from the following description of the preferred embodiment when considered in light of the drawings and the appended claims.

DETAILED DESCRIPTION OF THE INVENTION

Cartesian Coordinates

Figure 5:
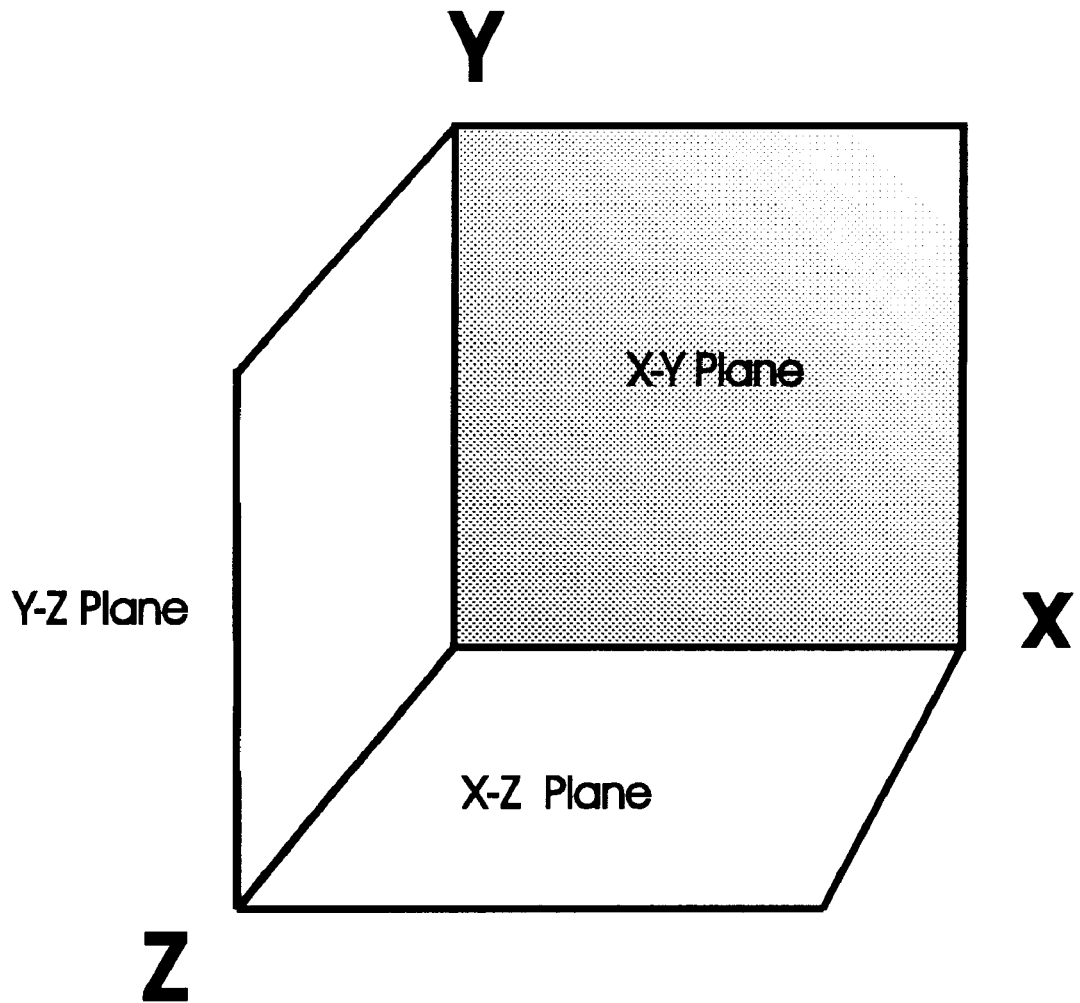
FIG. 5 shows a three dimensional cartesian coordinates system by which the three dimensional elements of the instant apparatus may be described.

A mathematical system has long since been devised for identifying elements in a set of points by labeling them with numbers. The numbers are called coordinates and can be thought of as giving the position of a point within the set. The system of latitude and longitude is an example of a coordinate system that uses two coordinates to specify the position of a point on the surface of the earth. The system of Cartesian coordinates is the most commonly used coordinate system. In two dimensions, this system consists of a pair of lines on a flat surface, or plane, that intersect at right angles. Each of the lines is called an axis and the point at which they intersect is called the origin. The axes are usually drawn horizontally and vertically and are usually referred to as the x and y axes, respectively. In Cartesian coordinates, a point on the plane whose coordinates are (2,3) is 2 units to the right of the y axis and 3 units up from the x axis, as. As shown in FIG. 5, in three-dimensional Cartesian coordinates, the z axis is added so that there are three axes all perpendicular to each other. The x, y and z axes are mutually perpendicular to each other, and can thus can more specifically be characterized as the intersections of the x-y, y-z and z-x planes. Furthermore, any point in a three-dimensional space may be described in terms of its projection on the x-y, y-z and z-x planes. Thus, a three dimensional object may be precisely described in terms of points and planes within, or passing through, the three dimensional space that it occupies.

The Apparatus

Figure 1A:
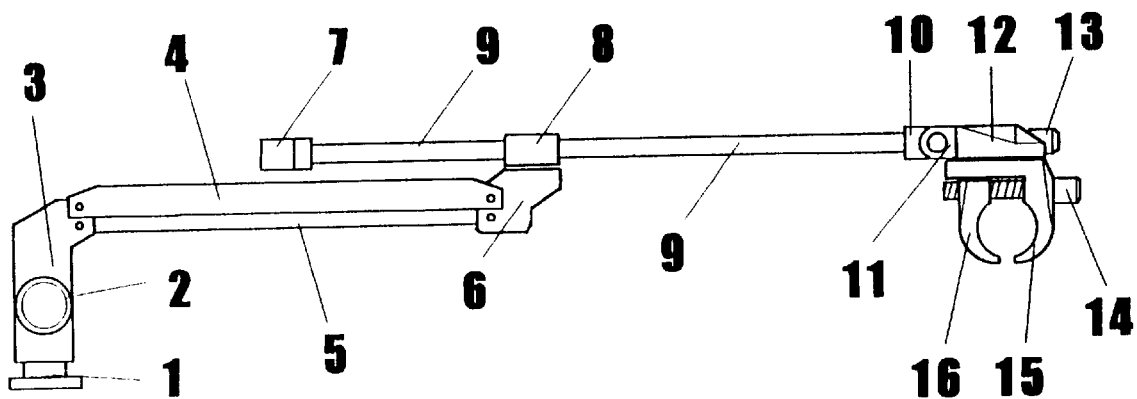
FIG. 1a shows an elevation view of the first side of the apparatus of the invention.
Figure 1B:
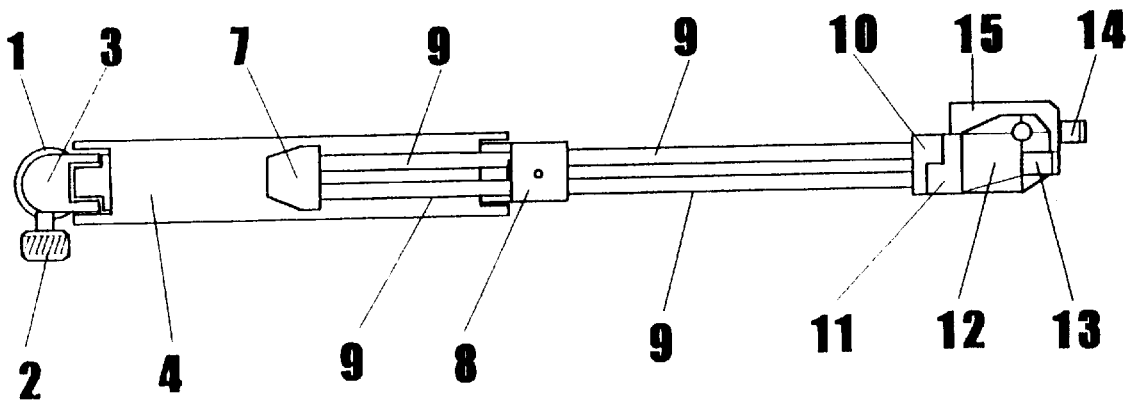
FIG. 1b shows a plan view of the apparatus of the invention.
Figure 3:
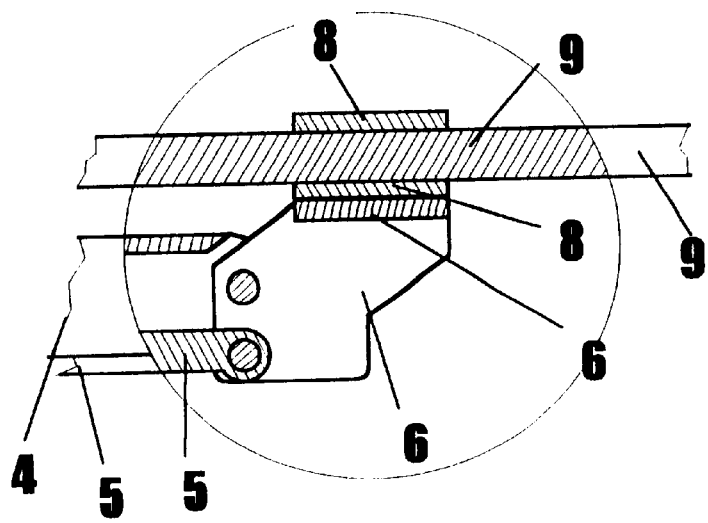
FIG. 3 shows a partial elevation view of the third portion of the adjustable arm of the apparatus of the invention.

Although the instant invention has broader application, it will be more specifically described with respect to its application to the dentistry arts. Referring to the drawings; the invention provides a parallelomete apparatus for cooperating with a dental hand drill. As shown in FIGS. 1a, 1b and 3; the hand drill includes a dental drill bit having a longitudinal axis. The apparatus functions to maintain substantially constant angles of the longitudinal axis of drill bit of the dental drill, in the X-Y, Y-Z and Z-X planes, as defined in part by the X, Y and Z axes, as the dental practitioner causes the drill to move through a volume of space. Typically, these angles are from about 8° to about 10°, but can range from about 3° to about 15°. Broadly, the apparatus includes: an adjustable arm having two ends; a clamp arrangement (14-16) for fixing the powered dental drill to one of the two ends; and, a base (1-2) fixable to a work piece, i.e., a palatal prosthesis or alternatively, hand held in the mouth of a dental patient; attached to the other of the two ends, for supporting the adjustable arm (4-13) and the clamp arrangement (14-16). For purposes of example only, where the work piece is a palatal prosthesis, the base of the instant apparatus may be fixed thereto by means of any conventional autopolymerizable polymer resin suitable for dental application, such as a polyacrylate. Still more specifically, the adjustable arm (4-13) further includes: an arrangement for vertical extension or retraction thereof The arrangement for vertical extension or retraction of the adjustable arm (4-13) still further includes an outer tube with an inner tube disposed therein, and a hole in the outer tube with a setscrew disposed therein for cooperating for selectively fixing the inner tube within the outer tube. In this manner the vertical length of the base component of the apparatus may be varied. In addition, the outer tube may be freely rotated about the inner tube and telescoped on the inner tube. This, in combination with the substantially free rotation enabled by the pin uniting the two parts of third portion (6, 8), permits the longitudinal axis of the dental drill bit to be maintained at a substantially constant angle, while being moved through 360° in a substantial volume of x-y planes. The adjustable arm (4-13) further includes: a first portion (4, 5) having two ends. The first portion (4, 5) functions for enabling vertical displacement of the longitudinal axis relative to the Y axis. The first portion (4, 5) further included two members of a major length and two members of a minor length, pinned at their respective ends. The members are deformable at the respective pins thereof, sufficient to form a structure that can be deformed to/from a generally rectangular shape to/from a parallelpiped shape. The adjustable arm (4-13) further includes: a second portion (7, 9 and 10-13) having two ends, for supporting the clamp arrangement (14-16); and, a third portion (6, 8) for movably fixing one end of the first portion to one end of the second portion.

The third portion further includes: a tube designed for slidably accommodating the second portion, there within (8), for horizontal extension and retraction of the second portion, generally relative to the X-Z plane; and, a pin for connecting the first arrangement to the second arrangement designed for enabling rotation of the first arrangement thereabout relative to the second arrangement (6), for enabling revolution of the clamp arrangement about the third portion. As noted above, the outer tube may be freely rotated about the inner tube and telescoped on the inner tube. In addition, substantially free rotation is enabled by the pin uniting the two parts of third portion (6, 8). These degrees of freedom permit the longitudinal axis of the dental drill bit to be maintained at a substantially constant angle, while being moved through 360° in a substantial volume of x-z planes. The clamp arrangement further includes: a first pivot arrangement (10-12) for enabling the clamp arrangement to be revolved thereabout in a substantially vertical plane; a clamp having a base; and, a second pivot arrangement for connecting the clamp to the first pivot arrangement and for enabling the clamp to be rotated thereabout.

Figure 2:
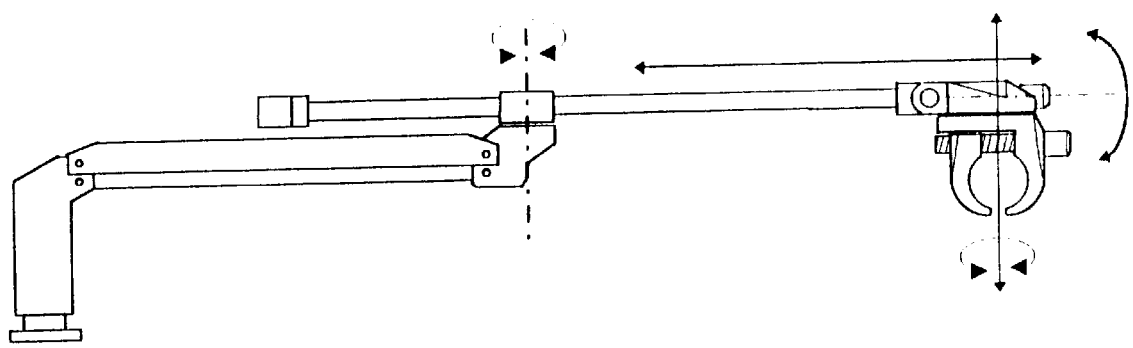
FIG. 2 shows a partial elevation view of the apparatus of the invention.

FIG. 2 shows the various degrees of freedom that the instant invention enables; i.e., the pivoting of the clamp assembly around the substantial midpoint of adjustable arm; the pivoting of the clamp assembly the vertical plane about one end of the adjustable arm; and, the pivoting of the clamp relative to the end of the adjustable arm.

FIG. 3 shows a partial elevation view of the third portion of the adjustable arm of the apparatus of the invention. More specifically, it shows a tube (8) designed for slidably accommodating the second portion (9), there within for horizontal extension and retraction of the second portion (9) relative to the X-Z plane; and, a pin (not shown) for connecting the first arrangement (8) to the second arrangement (6) designed for enabling rotation of the first arrangement (8) thereabout, relative to the second arrangement (6); for enabling revolution of the clamp arrangement about the third portion.

Figure 4:
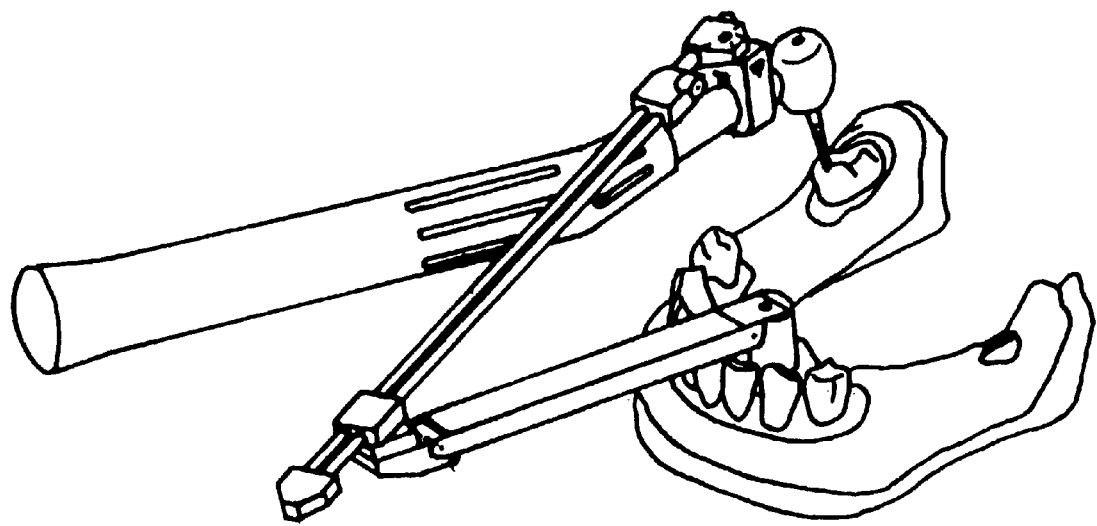
FIG. 4 shows an isometric view of the of the apparatus of the invention combined with a dental hand drill as applied to a palatal prothesis.

FIG. 4 shows the apparatus combined with a dental drill, used in operation on a palatal prosthesis.

The Method

The apparatus is fixed to the palatal prosthesis with i.e., autopolymerizable polyacrylate polymer resin, and the dental drill is clamped to the apparatus, as shown in FIG. 4. The apparatus is manipulated about its various pivot point as shown in FIG. 2, until the desired drill bit axis orientation is achieved as shown in FIG. 4. Although a slight error in the orientation of the drill bit axis occurs when the drill bit is moved from one point of the tooth in the prosthesis, to the other; the error is so slight as to be negligible. Thus, the relationship of the axis of the drill bit as between one point on a tooth to another is substantially parallel.

The apparatus has application either to the open mouth of a dental patient or substantially any dental operation conducted on a palatal prosthesis in a dental laboratory. While operating on the open mouth of a dental patient, the dentist fixes the base 1, with his thumb and fingers of one hand. In contrast, while operating on a palatal prosthesis, the base is preferably fixed to the prosthesis by means of any conventional autopolymerizable polymer resin suitable for dental application, such as a polyacrylate.

Although the invention has been described with reference to certain preferred embodiments, it will be appreciated that many variations and modifications may be made within the scope of the broad principles of the invention. Hence, it is intended that the preferred embodiments and all of such variations and modifications be included within the scope and spirit of the invention, as defined by the following claims.

I claim:

1. For cooperating with a powered tool that includes a work imparting component having a longitudinal axis; an apparatus for maintaining substantially constant angles of said longitudinal axis in the X-Y, Y-Z and Z-X planes, as defined in part by the X, Y and Z axes; as said powered tool is caused to move through a volume of space, comprising:

an adjustable arm having two ends;
   a clamp arrangement (14-16) for fixing said powered tool to one of said two ends; and,
   a base (1-2) fixable to a work piece, attached to the other of said two ends, for supporting said adjustable arm (4-13) and said clamp arrangement (14-16);
   wherein said adjustable arm further comprises:
      a first portion (4, 5) having two ends, for enabling vertical displacement of said longitudinal axis relative to the Y axis;
      a second portion (7, 9 and 10-13) having two ends, for supporting said clamp arrangement (14-16); and,
      a third portion (6, 8) for movably fixing one end of said first portion to one end of said portion; and
   wherein said base further comprises an arrangement for vertical extension or retraction thereof that includes an outer tube with an inner tube disposed therein, and a hole in said outer tube with a setscrew disposed therein for selectively fixing said inner tube within said outer tube.

2. The apparatus of claim 1, wherein said third portion further comprises:

a first arrangement (8) for horizontal extension and retraction of said second portion relative to said X-Z plane; and,
   a second arrangement (6) for enabling revolution of said clamp arrangement about said third portion.

3. The apparatus of claim 1, wherein said powered tool is a dental hand drill and said work imparting component is a dental drill bit.

4. The apparatus of claim 1, wherein said first portion (4, 5) further comprises two members of a major length and two members of a minor length, pinned at their respective ends sufficient to form a structure that can be deformed to/from a generally rectangular shape to/from a parallelpiped shape.

5. The apparatus of claim 1, wherein said first portion is a tube designed for slidably accommodating said second portion, there within.

6. The apparatus of claim 1, wherein said third portion further comprises a pivot pin for connecting said first arrangement to said second arrangement designed for enabling rotation of said first arrangement thereabout relative to said second arrangement.

7. The apparatus of claim 1, wherein said clamp arrangement further includes:

a first pivot arrangement (10-12) for enabling said clamp arrangement to be revolved thereabout in a vertical plane;
   a clamp having a base; and,
   a second pivot arrangement for connecting said clamp to said first pivot arrangement and for enabling said clamp to be rotated thereabout; and,
   said clap further comprises:
      a first substantially fixed clamp jaw;
      a second substantially movable clamp jaw; and, a screw arrangement for connecting said first substantially fixed clamp jaw and said second substantially movable clamp jaw; and for enabling movement of said second substantially movable clamp jaw toward said first substantially fixed clamp jaw sufficient for removably fixing said powered tool to said clamp arrangement.

8. For cooperating with a dental hand drill having a dental drill bit having a longitudinal axis; an apparatus for maintaining substantially constant angles of said longitudinal axis in the X-Y, Y-Z and Z-X planes, as defined in part by the X, Y and Z axes; as said powered tool is caused to move through a volume of space, comprising:

an adjustable arm having two ends;

a clamp arrangement (14-16) for fixing said powered tool to one of said two ends; and, a base (1-2) fixable to a work piece, attached to the other of said two ends, for supporting said adjustable arm (4-13) and said clamp arrangement (14-16); said base further comprising: an arrangement for vertical extension or retraction thereof, that further includes an outer tube with an inner tube disposed therein, and a hole in said outer tube with a setscrew disposed therein for cooperating for selectively fixing said inner tube within said outer tube;

wherein said adjustable arm further comprises:

a first portion (4, 5) having two ends, for enabling vertical displacement of said longitudinal axis relative to the Y axis, further including two members of a major length and two members of a minor length, pinned at their respective ends sufficient to form a structure that can be deformed to/from a generally rectangular shape to/from a parallelpiped shape;

a second portion (7, 9 and 10-13) having two ends, for supporting said clamp arrangement (14-16); and, a third portion (6, 8) for movably fixing one end of said first portion to one end of said second portion;

wherein said third portion further comprises:

a tube designed for slidably accommodating said second portion, there within (8) for horizontal extension and retraction of said second portion relative to said X-Z plane; and, a pivot pin for connecting said first arrangement to said second arrangement designed for enabling rotation of said first arrangement thereabout relative to said second arrangement (6) for enabling revolution of said clamp arrangement about said third portion.

9. A method for imparting work to a work piece comprising:

providing an apparatus for cooperating with a powered tool including a dental hand drill having a work imparting component including a dental drill bit having a longitudinal axis sufficient to maintain substantially constant angles of said longitudinal axis in the X-Y, Y-Z and Z-X planes, as defined in part by the X, Y and Z axes; as said powered tool is caused to move through a volume of space, including: an adjustable arm having two ends; a clamp arrangement (14-16) for fixing said powered tool to one of said two ends; said clamp further comprises: a first substantially fixed clamp jaw; a second substantially movable clamp jaw; and, a screw arrangement for connecting said first substantially fixed clamp jaw and said second substantially movable clamp jaw; and for enabling movement of said second substantially movable clamp jaw toward said first substantially fixed clamp jaw sufficient for removably fixing said powered tool to said clamp arrangement; and, a base (1-2) fixable to a work piece, attached to the other of said two ends, for supporting said adjustable arm (4-13); said base further comprising an arrangement for vertical extension or retraction thereof that includes an outer tube with an inner tube disposed therein, and a hole in said outer tube with a setscrew disposed therein for selectively fixing said inner tube within said outer tube; said clamp arrangement (14-16) further including: a first pivot arrangement (10-12) for enabling said clamp arrangement to be revolved thereabout in a vertical plane; a clamp having a base; said first pivot arrangement (10-12) being designed for enabling said clamp arrangement to be revolved thereabout; and, a second pivot arrangement for connecting said clamp to said first pivot arrangement and for enabling said clamp to be rotated thereabout; wherein said adjustable arm further comprises: a first portion (4, 5) having two ends, for enabling vertical displacement of said longitudinal axis relative to the Y axis; a second portion (7, 9 and 10-13) having two ends, for supporting said clamp arrangement (14-16); and, a third portion (6, 8) for movably fixing one end of said first portion to one end of said second portion; wherein said third portion further comprises: a first pivot arrangement (10-12) for enabling said clamp arrangement to be revolved thereabout in a vertical plane; a clamp having a base, and, a second pivot arrangement for connecting said clamp to said first pivot arrangement and for enabling said clamp to be rotated thereabout;

providing a work piece;

fixing said base to said work piece; and, manipulating said apparatus so as to apply work to said work piece through said work imparting component.

10. The method of claim 9, wherein said first portion (4, 5) further comprises two members of a major length and two members of a minor length, pinned at their respective ends sufficient to form a structure that can be deformed to/from a generally rectangular shape to/from a parallelpiped shape.

11. The method of claim 9, wherein said first arrangement is a tube designed for slidably accommodating said second portion, there within.

12. The method of claim 9, wherein said third portion further comprises a pivot pin for connecting said first arrangement to said second arrangement designed for enabling rotation of said first arrangement thereabout relative to said second arrangement.

13. The method of claim 9, wherein said clamp arrangement further includes:

a first pivot arrangement (10-12) for enabling said clamp arrangement to be revolved thereabout in a vertical plane;

a clamp having a base; and, a second pivot arrangement for connecting said clamp to said first pivot arrangement and for enabling said clamp to be rotated thereabout; and, said clamp further comprises:

a first substantially fixed clamp jaw;

a second substantially movable clamp jaw; and, a screw arrangement for connecting said first substantially fixed clamp jaw and said second substantially movable clamp jaw; and for enabling movement of said second substantially movable clamp jaw toward said first substantially fixed clamp jaw sufficient for removably fixing said powered tool to said clamp arrangement.

* * * * *